(12) United States Patent  (10) Patent No.: US 8,311,298 B2
Kim et al.  (45) Date of Patent: Nov. 13, 2012

(54) METHOD AND SYSTEM FOR PROCESSING VISUAL IMAGES OF DIGESTIVE SYSTEM

(75) Inventors: Young Ho Kim, Seoul (KR); Young Dae Seo, Seoul, KS (US); Dong Ha Lee, Seoul (KR); Jeongkyu Lee, Trumbull, CT (US)

(73) Assignee: Intromedic Co., Ltd., Seoul (KR)

( * ) Notice: Subject to any disclaimer, the term of this patent is extended or adjusted under 35 U.S.C. 154(b) by 706 days.

(21) Appl. No.: 12/334,423

(22) Filed: Dec. 12, 2008

(65) Prior Publication Data

US 2010/0150416 A1  Jun. 17, 2010

(51) Int. Cl.
*G06K 9/00* (2006.01)
(52) U.S. Cl. .................... 382/128; 600/109; 600/118
(58) Field of Classification Search .................. 382/128, 382/232; 600/109, 160, 407, 476, 117, 118, 600/424
See application file for complete search history.

(56) References Cited

U.S. PATENT DOCUMENTS

| | | | |
|---|---|---|---|
| 2005/0171418 A1* | 8/2005 | Lin | 600/407 |
| 2007/0268280 A1* | 11/2007 | Fujita et al. | 345/204 |
| 2007/0282169 A1* | 12/2007 | Tsujita | 600/160 |
| 2008/0112627 A1* | 5/2008 | Oda | 382/232 |
| 2009/0318761 A1* | 12/2009 | Rabinovitz | 600/118 |
| 2010/0268025 A1* | 10/2010 | Belson | 600/109 |
| 2010/0274083 A1* | 10/2010 | Hyoung et al. | 600/109 |
| 2011/0044515 A1* | 2/2011 | Spyridonos et al. | 382/128 |
| 2011/0060189 A1* | 3/2011 | Belson | 600/117 |

* cited by examiner

*Primary Examiner* — William C Dowling
(74) *Attorney, Agent, or Firm* — Edwards Wildman Palmer LLP

(57) ABSTRACT

The present invention provides a method and system for processing visual images of a digestive system. The method comprises: detecting visual images of a digestive system; storing the detected visual images; analyzing the stored visual images to identify corresponding event frames; and displaying the identified event frames quantitatively with respect to at least one reference. With the method and system, visual images of a digestive system can be processed more accurately, efficiently and conveniently for diagnostic purposes.

18 Claims, 11 Drawing Sheets

METHOD AND SYSTEM FOR PROCESSING VISUAL IMAGES OF DIGESTIVE SYSTEM

TECHNICAL FIELD

The present invention relates to a method and system for processing visual images of a digestive system for use in diagnosis.

BACKGROUND ART

A human digestive system consists of several different organs including esophagus, stomach, small intestine (i.e., duodenum, jejunum, and ileum) and colon. To date, various endoscopic methods such as gastroscopy and push enteroscopy colonoscopy have been used to visualize the human digestive system as a diagnostic tool. The prior art methods, however, do not visualize small intestine so as to fulfill the requirement to provide a precise diagnostic test.

One approach proposed to address the problem was to use Wireless Capsule Endoscopy (WCE), which integrates wireless transmission with image and video technology. In particular, WCE employs a small capsule (e.g., 11 mm in diameter and 24 mm in length). The small capsule includes a light emitting diode (LED) and a micro camera. The LED illuminates the luminal surface of a gut and the micro camera detects and sends images via wireless transmission to a receiver worn by a patient. The transmitted image data is transferred to a computer and specialists interpret the data for diagnostic purposes.

WCE, however, has drawbacks in that it takes long to read and interpret video images and it produces false-positive and/or false-negative errors.

There is thus a need for a new method and system for processing visual images of a digestive system more accurately, efficiently and conveniently.

The above information disclosed in this Background Art section is only for enhancement of understanding of the background of the invention and therefore it may contain information that does not form the prior art that is already known in this country to a person of ordinary skill in the art.

SUMMARY OF DISCLOSURE

In one aspect, the present invention provides a method for processing visual images of a digestive system. The method comprises: detecting visual images of a digestive system; storing the detected visual images; analyzing the stored visual images to identify corresponding event frames; and displaying the identified event frames quantitatively with respect to at least one reference.

In another aspect, the present invention provides a storage medium encoded with a machine-readable computer program for implementing the above-described method.

In a further aspect, the present invention provides a system for processing visual images of a digestive system, the system comprising: an image detection unit for detecting visual images of a digestive system; a data storage unit for storing the detected visual images; a processing unit for analyzing the visual images to identify corresponding event frames; and a displaying unit for displaying the identified event frames quantitatively with respect to at least one reference selected from the group comprising time and medical event.

It is understood that the term "digestive system" or other similar term as used herein is inclusive of digestive system of animals including human.

It is also understood that the term "visual image" or other similar term as used herein is inclusive of endoscope, colonoscopy, wireless capsule endoscope and wireless capsule colonoscopy video images.

It is also understood that the term "event frame" or other similar term as used here is inclusive of a sequence of visual images that include the same or similar semantic contents in, for example, endoscope, colonoscopy, wireless capsule endoscope and wireless capsule colonoscopy video images.

The above and other features of the invention are discussed infra.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION

Figure 1:
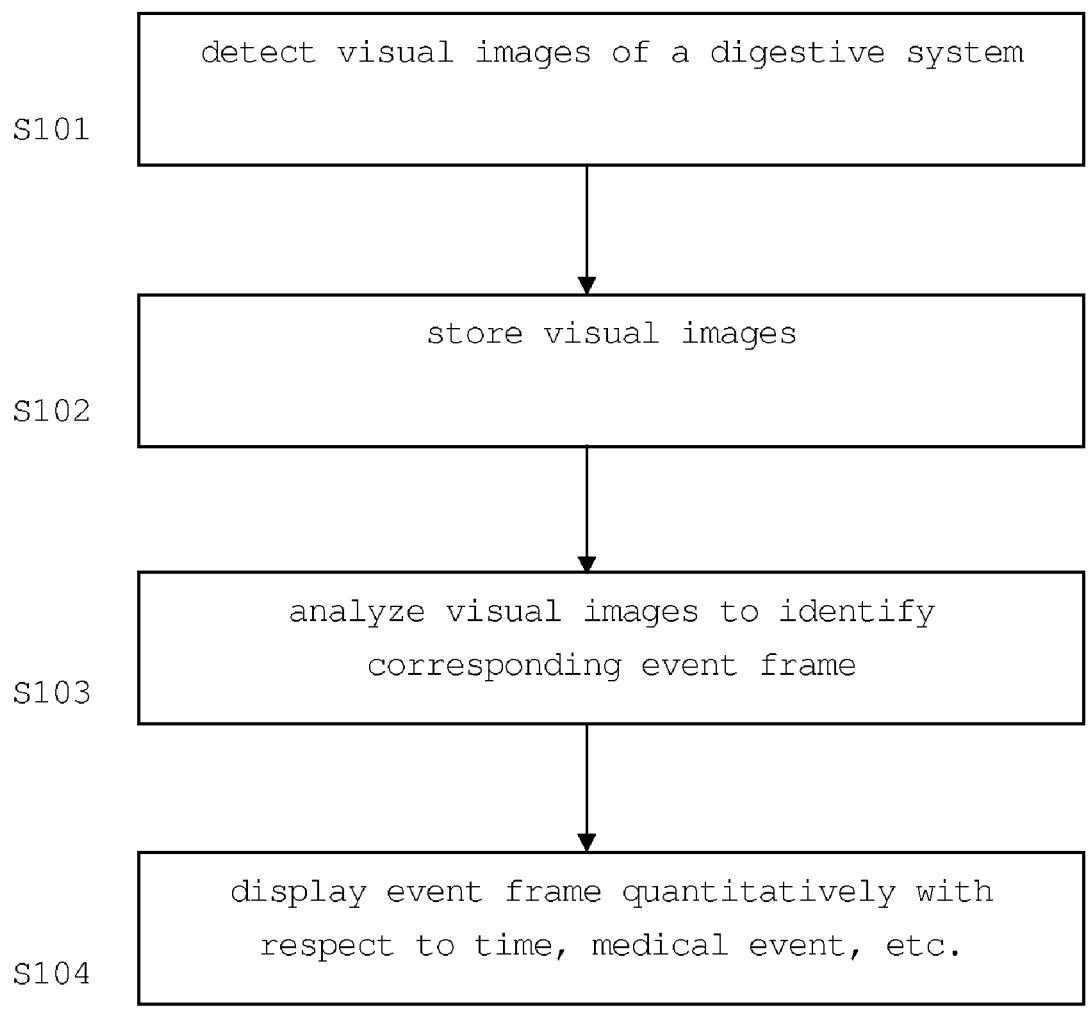
FIG. 1 is a flowchart illustrating a method for processing visual images of a digestive system according to an exemplary embodiment of the present invention.

Hereinafter, embodiments of the present invention will be described in detail with reference to the attached drawings. Reference should now be made to the drawings, in which the same reference numerals are used throughout the different drawings to designate the same or similar components.

As discussed above, one aspect of the present invention provides a method for processing visual images of a digestive system. For the purpose of illustration, a method for processing visual images of a human digestive system will be described with reference to FIGS. 1-9.

As shown in FIG. 1, visual images of a human digestive system are detected and stored in a workstation (S101, S102). More particularly, a patient swallows a small capsule that is equipped with a micro camera with a battery. The front end of the capsule has an optical dome where light emitting diodes (LEDs) illuminate the luminal surface of the digestive system, including gastrointestinal tract, or a part thereof and the micro camera sends captures images and send them via wireless transmission to a receiver disposed at a predetermined position (e.g., attached to a part of the body of a patient). As the capsule moves through the digestive system, visual images are transmitted by a digital radio frequency communication channel to a data recorder. The data are transferred to and stored in the workstation. The capsule is then passed in the patient's stool without the need for retrieval.

The stored visual images are analyzed to identify corresponding event frames (S103). The analysis of the visual images can be made by various methods. A preferred example of the methods is to recognize the contraction pattern of a digestive system. Also, the contraction pattern can be recognized by various methods including spectral analysis, motion flow analysis, shape analysis, wavelet analysis, frequency analysis and any combination thereof.

Contractions are intrinsic motility patterns in bowel movements, which is also the basic activity throughout entire gastrointestinal tract. Since the intestinal contraction is a very good pathological indicator, it is widely used for the diagnosis of gastrointestinal diseases. One of the examples using contractions is Electrogastrogram (EGG). EGG is a non-invasive recording of the electrical activity of stomach. Slow waves are generated from the activity of the gastrointestinal wall surface, or gastrointestinal contractions.

Figure 2A:
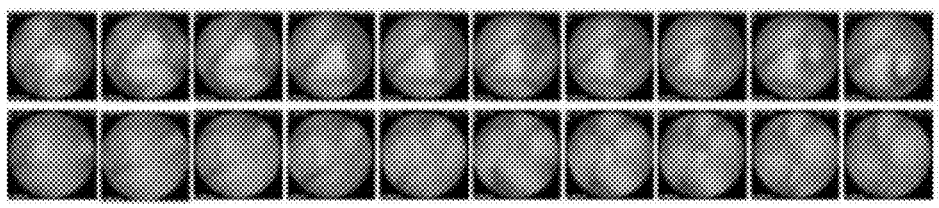
FIGS. 2A and 2B show sequences of image frames captured from stomach and small bowel, respectively, by WCE.
Figure 2B:
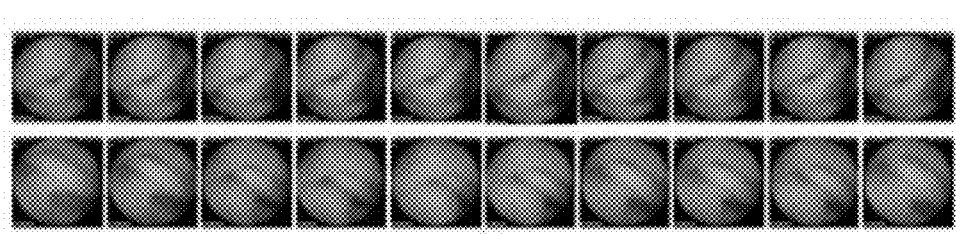

WCE videos can record continuous activities in a digestive system such as intestinal contractions, and visualize them easily. FIG. 2 shows examples of intestinal contractions taken by WCE. FIGS. 2A and 2B are sequences of frames captured from stomach and small bowel, respectively. As shown in FIGS. 2A and 2B, the motility patterns are different since different digestive organs have different types of movements and functionalities.

For example, energy-based feature in frequency domain from WCE images can be extracted, and then event boundaries can be detected by using a high frequency content (HFC) function to characterize the contractions and thereby identify medical events (See SAC '7 Mar. 11-15, 2007).

Figure 3:
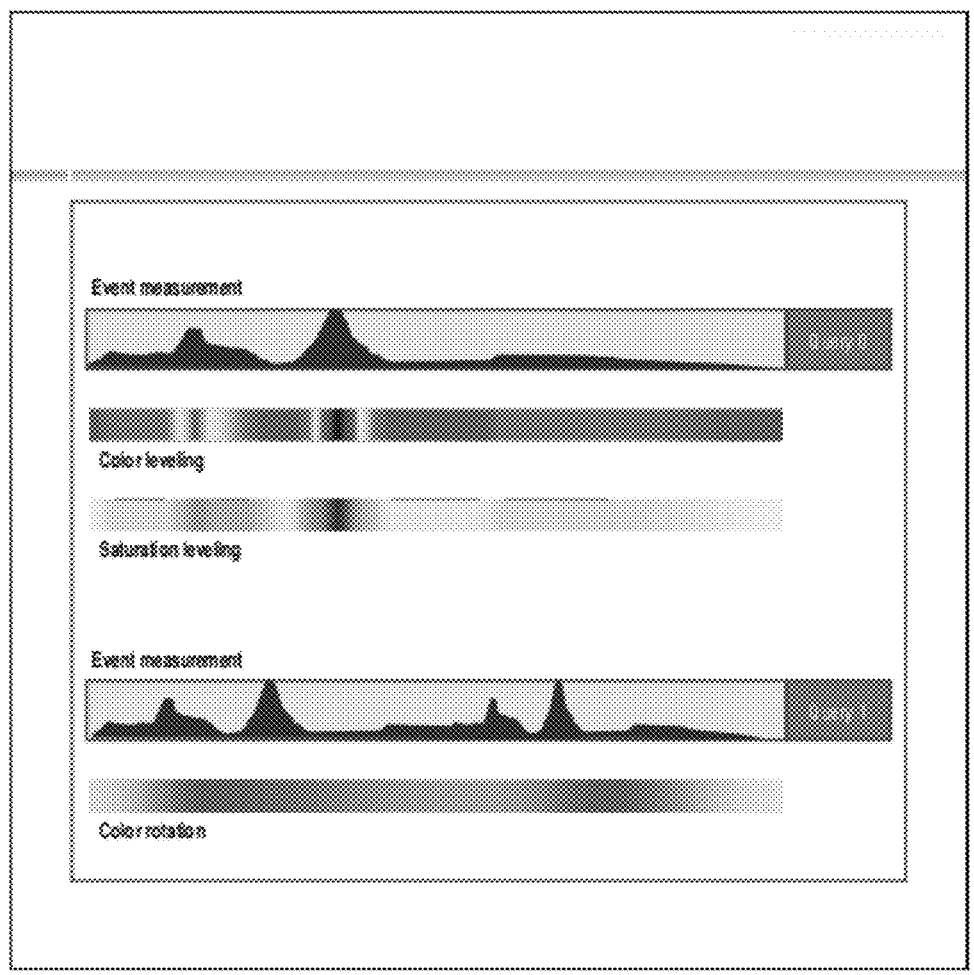
FIG. 3 shows an example of a screen displaying event frames in colorized bar and wave according to the present invention.
Figure 4:
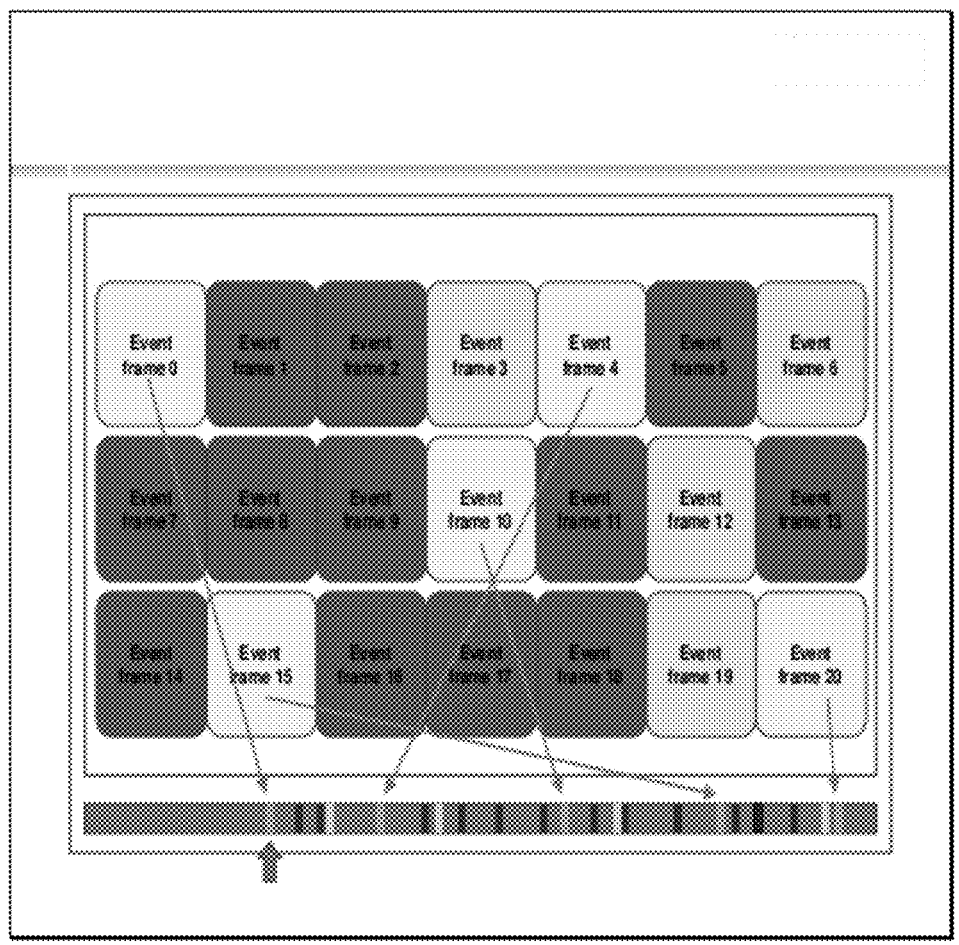
FIG. 4 shows an example of a screen displaying event frames along with time according to the present invention.
Figure 5:
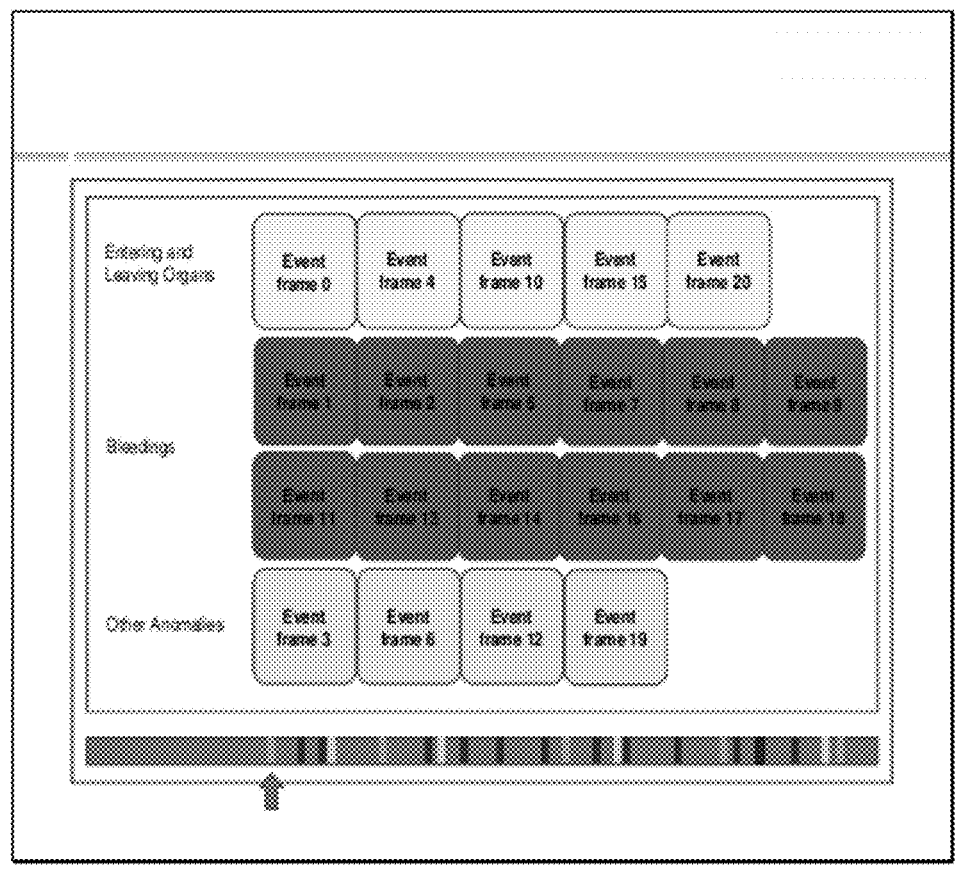
FIG. 5 shows an example of a screen displaying event frames by medical event category according to the present invention.

The thus identified event frames are displayed quantitatively with respect to various reference values including, for example, time, and medical event (S104). Any kind of methods that can display the medical events quantitatively can be used. Examples of such method include use of colorized bar, wave, and graphs. FIG. 3 shows an example of a screen displaying event frames in colorized bar and wave. Color leveling, saturation leveling, color rotations, or any combination thereof can be shown along with event measurement. Although both the colorized bar and wave are shown in FIG. 3, each of them can be used independently. Also, as shown in FIG. 4, event frames can be displayed along with time. In addition, as shown in FIG. 5, event frames can be displayed by medical event category. Preferably, the display modes of FIGS. 3-5 can be toggle-switched to each other. Also, they can be combined to produce a different display mode.

Figure 6:
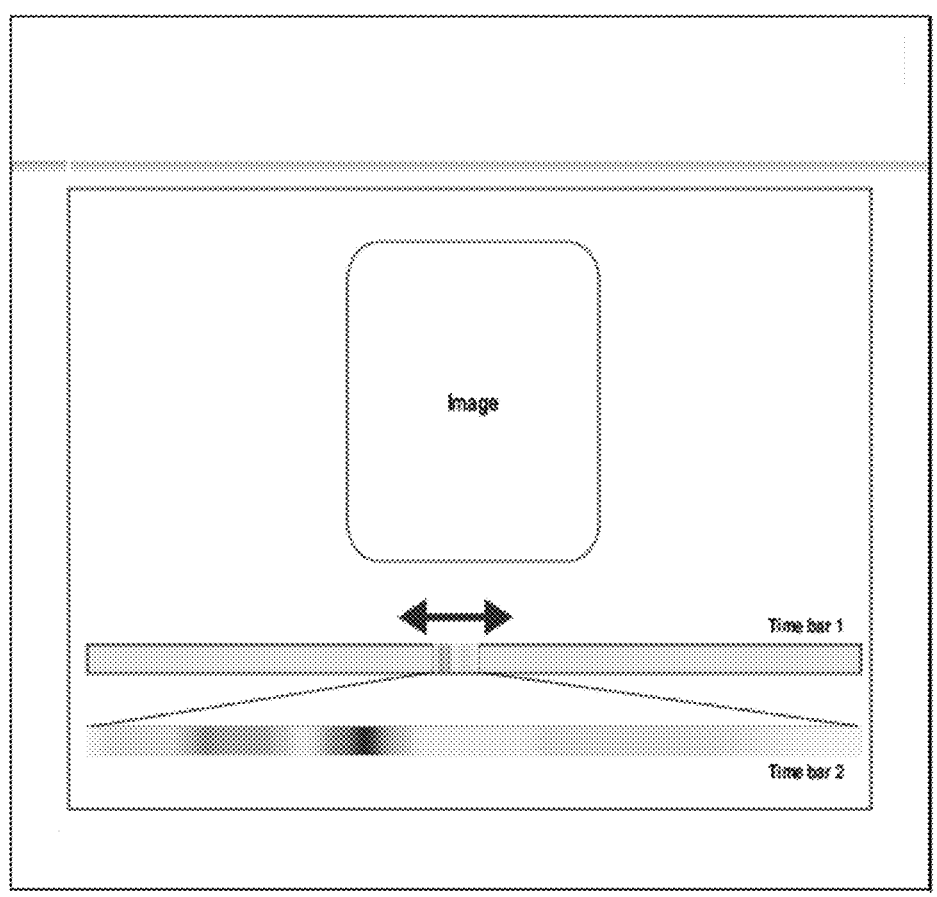
FIG. 6 shows an example of a screen displaying event frames with hierarchical coarse-to-fine view according to the present invention.

In an embodiment, event frames can be displayed with hierarchical coarse-to-fine images. For example, as shown in FIG. 6, event frames can be displayed with respect to time bars 1 and 2. The time bar 1 is used as a reference to display key image or images for a selected time window. The time bar 2 is used as a reference to display a plurality of images for the selected time window.

Figure 7:
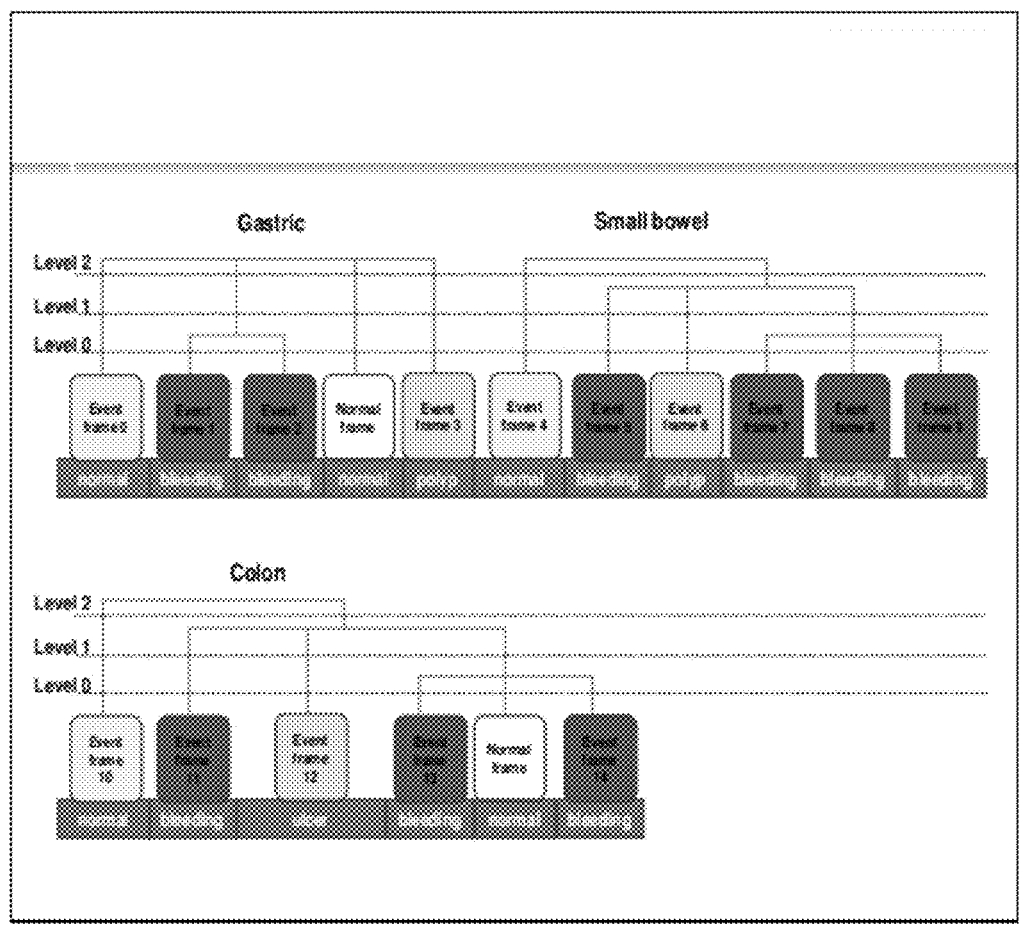
FIG. 7 shows an example of a screen displaying event frames at three levels according to the present invention.

Suitably, event frames can be displayed at a plurality of levels. For instance, as shown in FIG. 7, event frames are displayed at three levels. In particular, all event frames except for ones corresponding normal medical events with respect to respective digestive organs are displayed at level one, all event frames including ones corresponding normal medical events are displayed at level two, and event frames corresponding to key medical events are displayed at level three.

Figure 8:
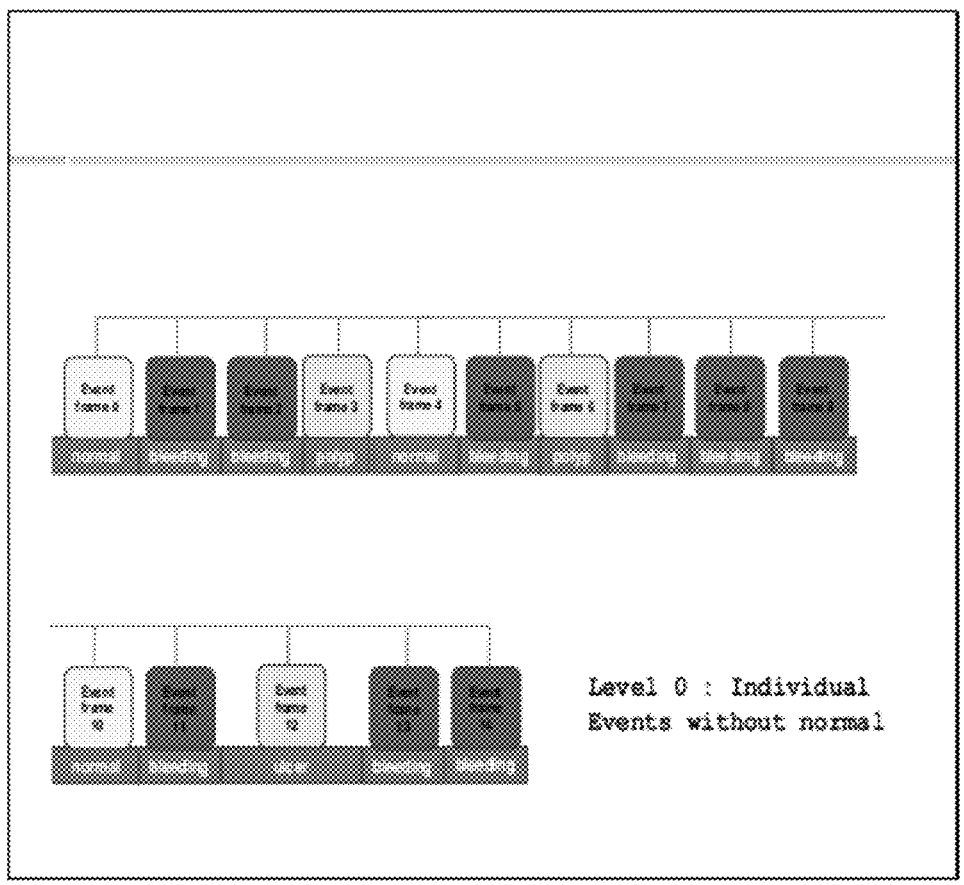
FIG. 8 shows an example of a screen displaying event frames at level one of FIG. 7.
Figure 9:
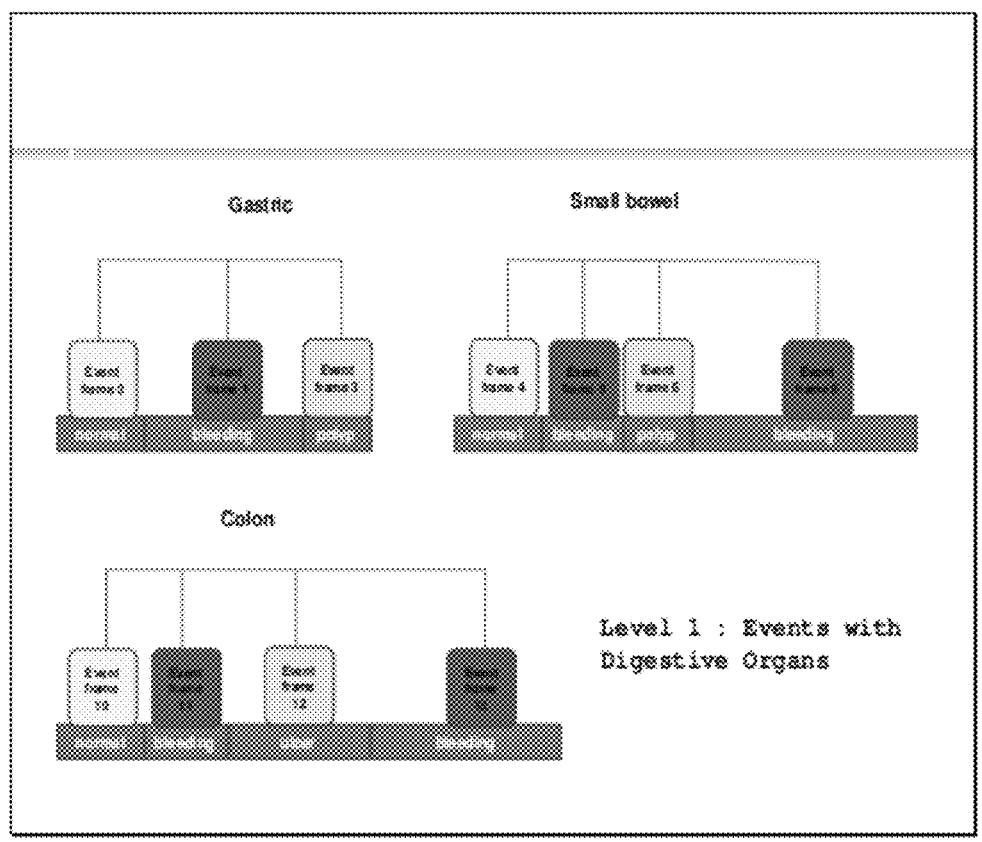
FIG. 9 shows an example of a screen displaying event frames at level two of FIG. 7.
Figure 10:
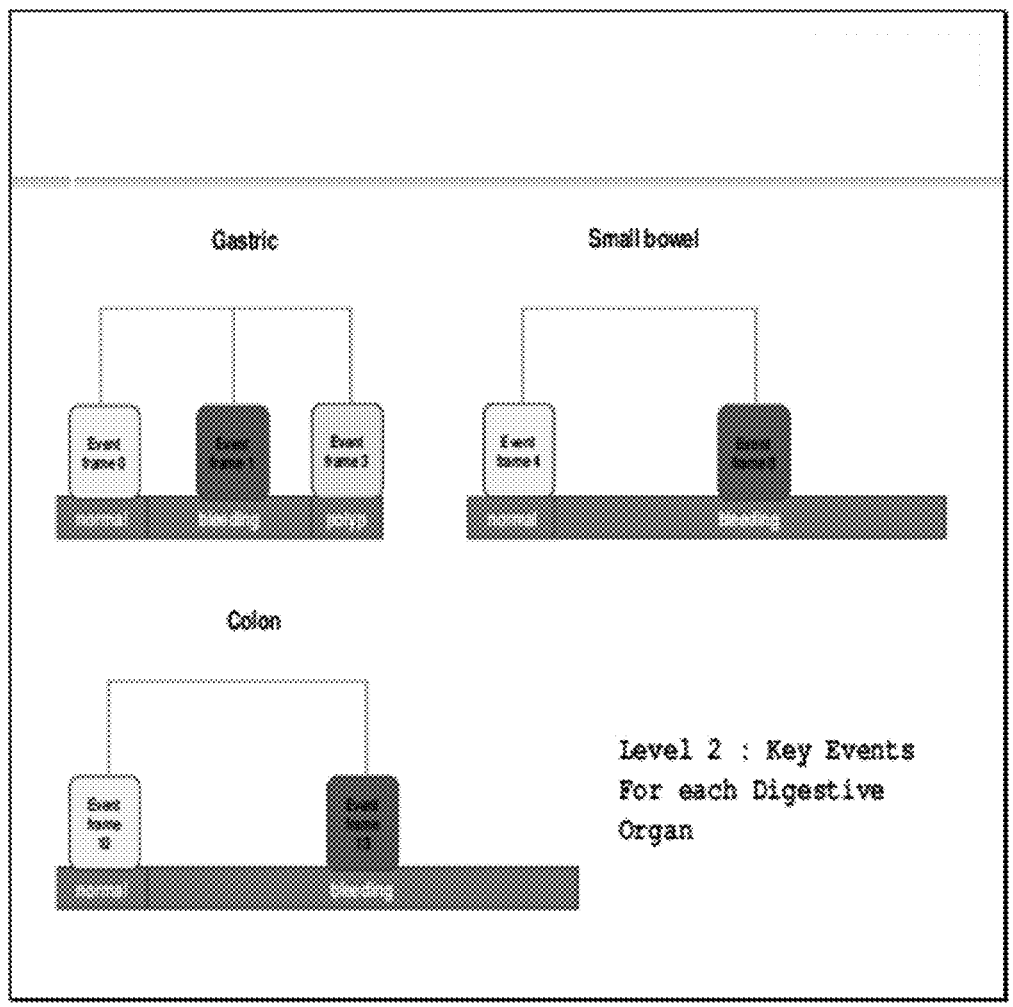
FIG. 10 shows an example of a screen displaying event frames at level three of FIG. 7.
Figure 11:
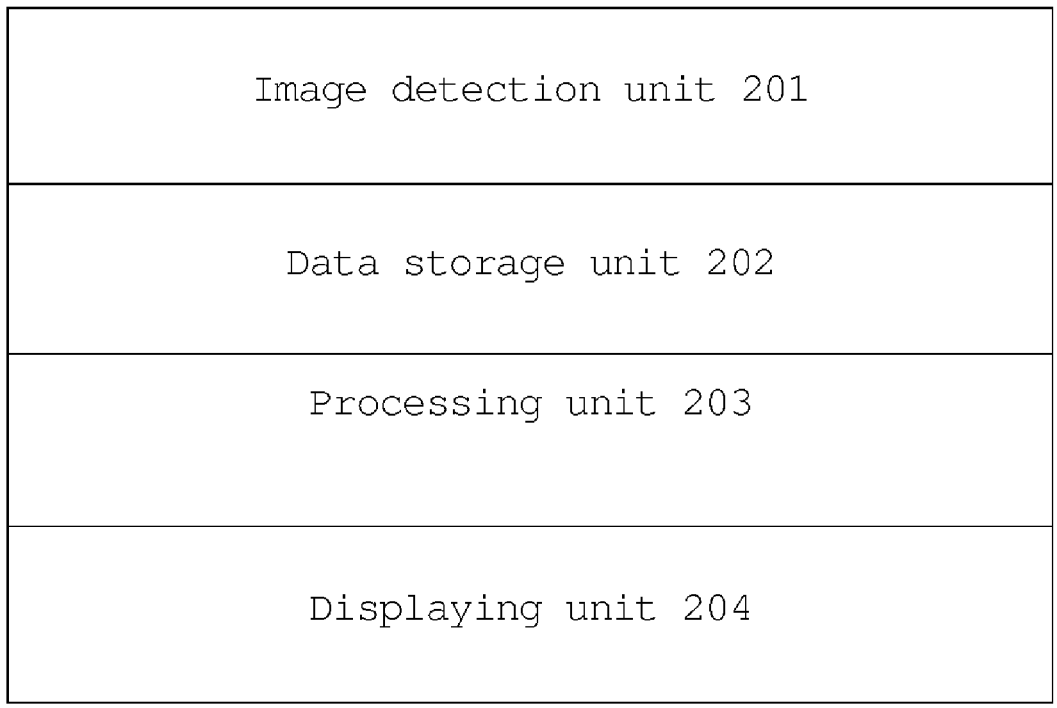
FIG. 11 is a diagram showing a system for processing visual images of a digestive system according to an embodiment of the present invention.
Figure 11:
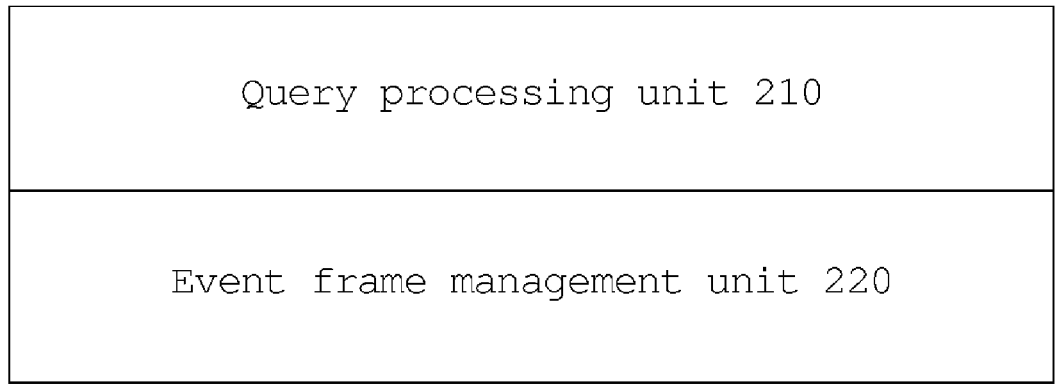

FIGS. 8-10 show examples of screen displaying event frames at level one, two and three of FIG. 7, respectively.

In a modified embodiment, a query can be received from a user and processed. For example, as shown in FIG. 3, a query window or section can be provided to a user. The query window or section provides items including, for example, organs, medical events, and display modes. If a user selects "small bowel," an event frame or frames detected in small bowel are displayed. If the user selects "bleeding," an event frame or frames detected as bleeding for respective organs are displayed. If the user selects a different display mode, selected display mode is provided to the user. Preferably, the display modes shown in FIGS. 3-10 can be toggle-switched. Although the query window or section is described only in FIG. 3, it can be provided in the other display modes of FIGS. 4-10.

In another modified embodiment, a reference abnormal image or images or a voice comment or comments for an identified event frame or frames can be stored and provided to a user. The image and voice information help the user read visual images more accurately, efficiently and conveniently.

As discussed above, another aspect of the present invention provides a computer-readable storage medium encoded with a computer program for implementing the above-described methods. The computer program may be recorded in computer-readable media including program instructions to implement various operations embodied by a computer. The media may also include, alone or in combination with the program instructions, data files, data structures, and the like. The media and program instructions may be those specially designed and constructed for the purposes of the present invention, or they may be of the kind well-known and available to those having skill in the computer software arts. Examples of computer-readable media include magnetic media such as hard disks, floppy disks, and magnetic tape; optical media such as CD ROM disks and DVD; magneto-optical media such as optical disks; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described exemplary embodiments of the present invention.

A further aspect of the present invention provides a system for processing visual images of a digestive system. The system 200 comprises an image detection unit 201, a data storage unit 202, a processing unit 203, and a displaying unit 204.

The image detection unit 201 detects visual images of a digestive system and the data storage unit 202 stores the detected visual images. For example, the image detection unit 201 can be realized as a small capsule including a micro camera, an optical dome having LEDs, and a battery. The LEDs illuminate the luminal surface of a digestive system including gastrointestinal tract, and the micro camera sends images via wireless transmission to a receiver disposed at a predetermined position (e.g., attached to a part of the body of a patient). As the capsule moves through the digestive system, images are transmitted by the digital radio frequency communication channel to a data recorder. The data are transferred to and stored in a workstation.

The processing unit 203 analyzes the visual images to identify corresponding event frames. As discussed above, the analysis of the visual images can be made by various methods. A preferred example of the methods is to recognize contraction pattern of a digestive system. Also, the contraction pattern can be recognized by various methods including spectral analysis, motion flow analysis, shape analysis, wavelet analysis, frequency analysis and any combination thereof.

The displaying unit 204 displays the identified event frames quantitatively with respect to various references such as time, medical event, etc. (FIGS. 4 and 5). As discussed above, any kind of method that can display the event frames quantitatively can be used. Examples of such method include use of colorized bar, wave, and graphs (FIG. 3).

Preferably, the displaying unit 204 displays event frames with hierarchical coarse-to-fine images. For example, as shown in FIG. 6, event frames with hierarchical coarse-to-fine images can be displayed with respect to time bars 1 and 2. The time bar 1 is used as a reference to display key image or images for a selected time window. The time bar 2 is used as a reference to display a plurality of images for the selected time window.

Suitably, the displaying unit 204 displays event frames at a plurality of levels. For instance, as shown in FIG. 7, event frames are displayed at three levels. In particular, all event frames except for ones corresponding normal medical events with respect to respective digestive organs are displayed at level one, all event frames including ones corresponding normal medical events are displayed at level two, and event frames corresponding to key medical events are displayed at level three. FIGS. 8-10 show examples of screen displaying event frames at level one, two and three of FIG. 7, respectively.

A modified embodiment of the above-described systems may further include a query processing unit 210. The query processing unit 210 receives a query from a user and processes the query accordingly. For example, as shown in FIG. 3, a query window or section can be provided to a user. The query window or section provides items including, for example, organs, medical events, and display modes. If a user selects "small bowel," an event frame or frames detected in small bowel are displayed. If the user selects "bleeding," an event frame or frames detected as bleeding for respective organs are displayed. If the user selects a different display mode, selected display mode is provided to the user. Preferably, the display modes shown in FIGS. 3-10 can be toggle-switched. Although the query window or section is described only in FIG. 3, it can be provided in the other display modes of FIGS. 4-10.

Another modified embodiment may further include an event frame management unit 220. The event frame management unit 220 stores a reference abnormal image or images or a voice comment or comments for an identified event frame or frames and provides the information to a user. The information helps the user read visual images more accurately, efficiently and conveniently.

In still another modified embodiment, the data storage unit 202 and/or the processing unit 203 can perform the function of the query processing unit 210 and the event frame management unit 220.

As described above, according to the present invention, visual images of a digestive system can be processed more accurately, efficiently and conveniently for diagnostic purposes.

Although the preferred embodiments of the present invention have been disclosed for illustrative purposes, those skilled in the art will appreciate that various modifications, additions and substitutions are possible, without departing from the scope and spirit of the invention as disclosed in the accompanying claims. The scope of the present invention is defined by the accompanying claims.

The invention claimed is:

1. A method for processing visual images of a digestive system, the method comprising:
   detecting visual images of a digestive system;
   storing the detected visual images;
   analyzing the stored visual images to identify corresponding event frames and medical events associated with each event frame by recognizing a contraction pattern of the digestive system wherein a medical event is at least one of a normal event, a bleeding event or an ulcer event; and
   displaying the identified event frames quantitatively organized based on one or more identified medical events identified by the analyzing the event frames.

2. The method of claim 1, wherein event frames are displayed quantitatively with respect to both medical events and time.

3. The method of claim 1, wherein the visual images are analyzed by spectral analysis, motion flow analysis, shape analysis, wavelet analysis, frequency analysis or any combination thereof.

4. The method of claim 1, wherein the event frames are displayed by colorized bar, wave, or both.

5. The method of claim 1, further comprising displaying event frames with hierarchical coarse-to-fine images.

6. The method of claim 1, further comprising displaying event frames at a plurality of levels.

7. The method of claim 6, wherein the event frames are displayed such that all event frames except for ones corresponding normal medical events with respect to respective digestive organs are displayed at level one, all event frames including ones corresponding normal medical events are displayed at level two, and event frames corresponding to key medical events are displayed at level three.

8. The method of claim 1, further comprising receiving and processing a query from a user.

9. The method of claim 1, further comprising storing a reference abnormal image or images or voice comment or comments for an event frame or frames.

10. A computer-readable storage medium encoded with a computer program for implementing a method for processing visual images of a digestive system, the method comprising:
    detecting visual images of a digestive system;
    storing the detected visual images;
    analyzing the stored visual images to identify corresponding event frames and medical events associated with each event frame by recognizing a contraction pattern of the digestive system wherein a medical event is at least one of a normal event, a bleeding event or an ulcer event; and
    displaying the identified event frames quantitatively organized based on one or more identified medical events identified by analyzing the event frames.

11. A system for processing visual images of a digestive system, the system comprising:
    an image detection unit configured to detect visual images of a digestive system;
    a data storage unit configured to store the detected visual images;
    a processing unit configured to analyze the visual images to identify corresponding event frames and medical events associated with each event frame by recognizing a contraction pattern of the digestive system wherein a medical event is at least one of a normal event, a bleeding event or an ulcer event; and a displaying unit configured to display the identified event frames quantitatively organized based on one or more identified medical events identified by the analysis of the event frames.

12. The system of claim 11, wherein the processing unit analyzes the visual images by spectral analysis, motion flow analysis, shape analysis, wavelet analysis, frequency analysis or any combination thereof.

13. The system of claim 11, wherein the displaying unit displays the event frames by colorized bar, wave or both.

14. The system of claim 11, wherein the displaying unit displays event frames with hierarchical coarse-to-fine images.

15. The system of claim 11, wherein the displaying unit displays event frames at a plurality of levels.

16. The system of claim 15, wherein the event frames are displayed such that all event frames except for ones corresponding normal medical events with respect to respective digestive organs are displayed at level one, all event frames including ones corresponding normal medical events are displayed at level two, and event frames corresponding to key medical events are displayed at level three.

17. The system of claim 11, further comprising a query processing unit for receiving and processing a query from a user.

18. The system of claim 11, further comprising an event frame management unit for storing a reference abnormal image or images or voice comment or comments for an event frame or frames.

* * * * *